United States Patent
Bharat et al.

(10) Patent No.: US 10,506,947 B2
(45) Date of Patent: Dec. 17, 2019

(54) AUTOMATED SELECTION OF OPTIMAL CALIBRATION IN TRACKED INTERVENTIONAL PROCEDURES

(71) Applicant: KONINKLIJKE PHILIPS N.V., Eindhoven (NL)

(72) Inventors: Shyam Bharat, Arlington, MA (US); Ananth Ravi, Toronto (CA); Ehsan Dehghan Marvast, New York, NY (US); Cynthia Ming-Fu Kung, New York, NY (US); Jochen Kruecker, Washington, DC (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 270 days.

(21) Appl. No.: 15/534,513

(22) PCT Filed: Nov. 23, 2015

(86) PCT No.: PCT/IB2015/059025
§ 371 (c)(1),
(2) Date: Jun. 9, 2017

(87) PCT Pub. No.: WO2016/092395
PCT Pub. Date: Jun. 16, 2016

(65) Prior Publication Data
US 2017/0354346 A1    Dec. 14, 2017

Related U.S. Application Data

(60) Provisional application No. 62/090,579, filed on Dec. 11, 2014.

(51) Int. Cl.
*A61B 5/06* (2006.01)
*A61N 5/10* (2006.01)

(52) U.S. Cl.
CPC ............ *A61B 5/062* (2013.01); *A61N 5/1001* (2013.01); *A61N 5/1027* (2013.01);
(Continued)

(58) Field of Classification Search
CPC ............ A61B 2560/0223; A61B 5/062; A61N 2005/1074; A61N 5/1075
(Continued)

(56) References Cited

U.S. PATENT DOCUMENTS 6,335,617 B1 *  1/2002  Osadchy ................. A61B 5/06
                                                            324/202
7,809,421 B1 * 10/2010  Govari .................. G01V 13/00
                                                            324/200
(Continued)

FOREIGN PATENT DOCUMENTS

WO    2013140315 A1    9/2013

*Primary Examiner* — John E Breene
*Assistant Examiner* — Jeffrey P Aiello (57) ABSTRACT

A system for selecting a calibration includes a data structure (138) including non-transitory computer readable storage media having a plurality of calibration entries stored therein and indexed to position and/or orientation criteria for a field generator. The field generator is configured for placement in an environment for sensor tracking. A calibration selection module (140) is configured to determine a position and/or orientation of the field generator and, based on the position and/or orientation, determine, using the data structure, corresponding calibration information stored in the data structure. The calibration information is optimized based upon the position and/or orientation of the field generator.

19 Claims, 5 Drawing Sheets

(52) U.S. Cl.
CPC ......... *A61N 5/1049* (2013.01); *A61N 5/1075* (2013.01); *A61B 2560/0223* (2013.01); *A61N 2005/1022* (2013.01); *A61N 2005/1051* (2013.01); *A61N 2005/1058* (2013.01); *A61N 2005/1074* (2013.01)

(58) Field of Classification Search
USPC ........ 324/202, 207.11; 700/258; 702/85, 94, 702/104, 151, 154, 95, 152, 153
See application file for complete search history.

(56) References Cited

U.S. PATENT DOCUMENTS

| | | | |
|---|---|---|---|
| 8,948,081 B2 | 2/2015 | Sudak et al. | |
| 2006/0167643 A1* | 7/2006 | Casto | G01R 35/005 702/85 |
| 2011/0054304 A1* | 3/2011 | Markowitz | A61B 90/13 600/424 |
| 2012/0022780 A1* | 1/2012 | Kulik | G01C 21/28 701/498 |
| 2013/0238128 A1* | 9/2013 | Suzuki | B25J 9/1669 700/258 |
| 2014/0142438 A1* | 5/2014 | Ludwin | A61B 5/0053 600/481 |
| 2014/0188422 A1* | 7/2014 | Huber | G01R 35/00 702/104 |
| 2015/0167447 A1* | 6/2015 | Tjhang | E21B 47/0002 348/85 |
| 2016/0082597 A1* | 3/2016 | Gorshechnikov | G06N 5/02 700/253 |
| 2017/0014192 A1* | 1/2017 | Bharat | A61B 17/3403 |

* cited by examiner

AUTOMATED SELECTION OF OPTIMAL CALIBRATION IN TRACKED INTERVENTIONAL PROCEDURES

CROSS-REFERENCE TO PRIOR APPLICATIONS

This application is the U.S. National Phase application under 35 U.S.C. § 371 of International Application Serial No. PCT/IB2015/059025, filed on Nov. 23, 2015, which claims the benefit of U.S. Application Ser. No. 62/090,579, filed on Dec. 11, 2014. These applications are hereby incorporated by reference herein.

BACKGROUND

Technical Field

This disclosure relates to device tracking instruments and more particularly to systems and methods for determining an optimal calibration for a position of a field generator for a tracking system.

Description of the Related Art

In interventional procedures involving any form of electromagnetic (EM) navigation/guidance, an EM field generator (FG) is provided near an area of the procedure and, in particular, close to where the tracking takes place. This may include a tracked area of interest, such as, e.g., a groin area in the case of prostate brachytherapy. The FG is usually supported by a mounting arm attached to a patient table. The FG may be parallel to the table, perpendicular to the table or angled towards the area of interest (e.g., the prostate), etc. Other factors that may influence positioning of the FG include patient-specific geometry (e.g., patient size, girth, etc.) and equipment/platform set-ups (e.g., positions of other essential clinical equipment such as leg stirrups in prostate brachytherapy, etc.).

Due to inter-patient size variation and other clinical factors, it may not be possible to achieve a same FG position and orientation in all clinical procedures as in a controlled setting during calibration. This may result in inaccurate electromagnetic to ultrasonic (EM-US) fusion during the interventional procedure since validity of the calibration is dependent on treatment geometry. If the position and orientation of the EM field generator (FG) with respect to the tracked EM sensors/tools is different from that during the calibration process, system performance will be sub-optimal and hence, there may be errors in therapy delivery.

SUMMARY

In accordance with the present principles, a system for selecting a calibration includes a data structure including non-transitory computer readable storage media having a plurality of calibration entries stored therein and indexed to position and/or orientation criteria for a field generator. The field generator is configured for placement in an environment for sensor tracking. A calibration selection module is configured to determine a position and/or orientation of the field generator and, based on the position and/or orientation, determine, using the data structure, corresponding calibration information stored in the data structure. The calibration information is optimized based upon the position and/or orientation of the field generator.

Another system for selecting a calibration includes a data structure including non-transitory computer readable storage media having a plurality of calibration entries stored therein and indexed to position and/or orientation criteria for a field generator, the field generator configured for placement in an environment for electromagnetic sensor tracking. A calibration selection module is configured to determine a position and/or orientation of the field generator and, based on the position and/or orientation, determine, using the data structure, corresponding calibration information stored in the data structure, the calibration information being optimized based upon the position and/or orientation of the field generator. A registration module is configured to register at least two coordinate systems using the calibration information, the two coordinate systems including at least a coordinate system for the sensor tracking and an imaging system.

A method for selecting a calibration includes monitoring a position and orientation of a reference sensor relative to a field generator; matching the position and orientation of the reference sensor to a calibration entry stored in a data structure, the data structure including non-transitory computer readable storage media; and outputting corresponding calibration information stored in the data structure, the calibration information being optimized based upon the position and orientation of the field generator.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

In accordance with the present principles, systems and methods provide accurate and robust placement of a field generator (FG) that is insensitive to position and orientation to ensure clinical acceptability. In one embodiment, a system automatically chooses an optimal calibration from a pre-populated database of calibrations, based on the patient-specific treatment geometry. Methods for determining the optimal calibration are also provided.

In an offline (pre-treatment) procedure, multiple calibrations are computed and stored in a database, each at a different position and/or orientation of the FG. The database is extensively populated with calibrations for multiple clinically-achievable FG positions and orientations. Each calibration in the database is tagged with a position and orientation of a 6 degree-of-freedom (DOF) reference sensor with respect to the FG. The reference sensor is attached at a permanent static location (e.g., on a stepper, for prostate brachytherapy procedures).

During a subsequent tracked interventional procedure, the FG is adjusted by the operator to a desired position and orientation (e.g., as dictated by the convenience of the operator). The system logs the position and orientation of the reference sensor (with respect to the FG) at that FG location and finds a best match tag from the database. The calibration corresponding to that tag is then automatically chosen as the optimal calibration to use for that treatment geometry. In one embodiment, the system continuously chooses the optimal calibration in real-time. Therefore, at any given instant, the calibration is optimal and fusion between tracking devices (electromagnetic trackers) and images (ultrasound (US)) is always accurate. In another embodiment, the system chooses the optimal calibration when initiated by the operator (e.g., via clicking a button, etc. on a user interface). The system ensures improved accuracy even if clinical constraints prohibit the positioning of the FG at a same location as that during calibration and/or if the position/orientation of the FG changes during the interventional procedure.

It should be understood that the present invention will be described in terms of medical instruments, and, in particular, EM tracking with ultrasound (US) (EM-US fusion); however, the teachings of the present invention are much broader and are applicable to any field generated tracking system and/or imaging system. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, prostate, kidneys, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W), Blu-Ray™ and DVD.

Figure 1:
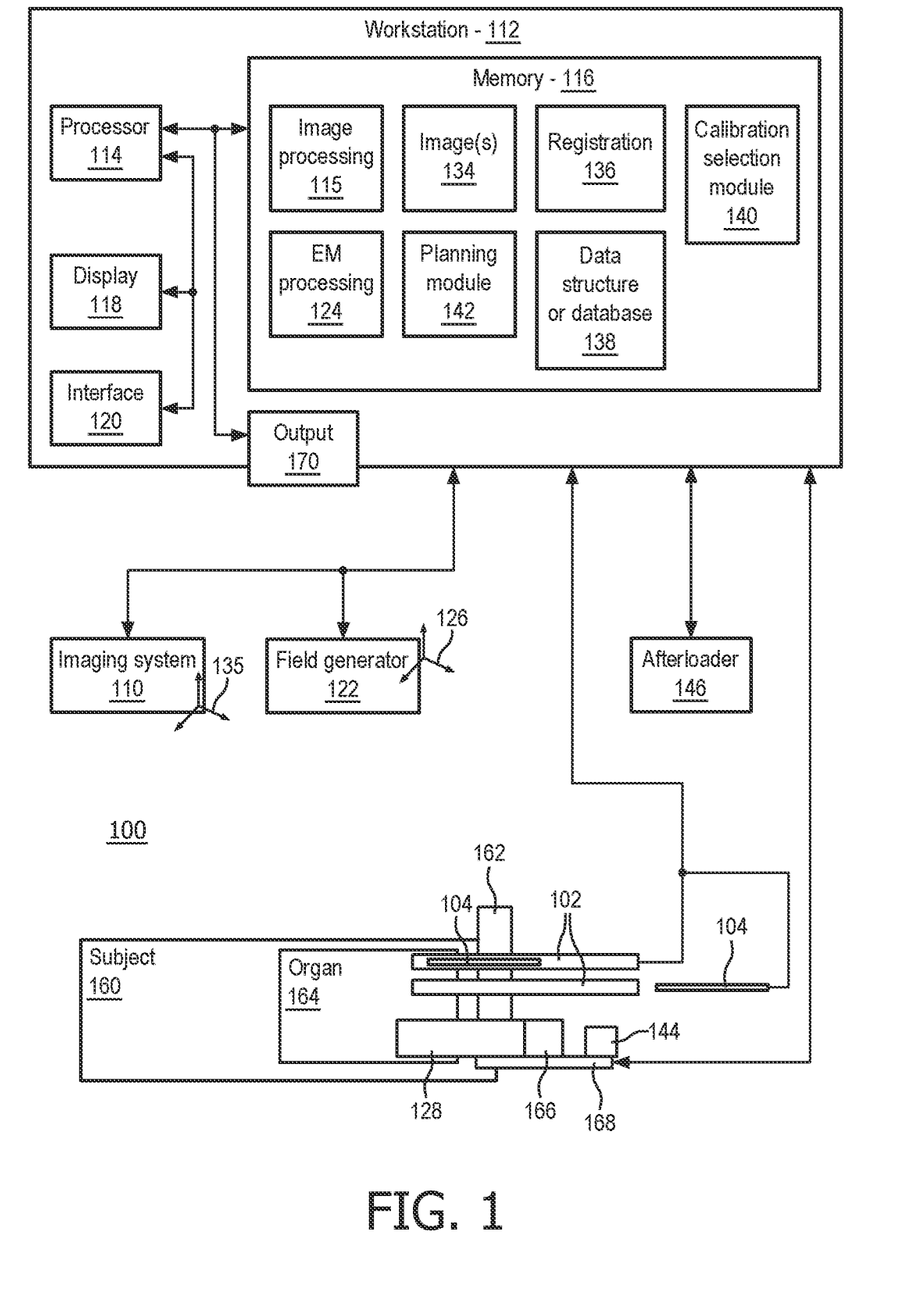
FIG. 1 is a block/flow diagram showing a system for calibrating a field generator in accordance with one embodiment.

Referring now to the drawings in which like numerals represent the same or similar elements and initially to FIG. 1, a system 100 for optimal placement of a field generator 122 is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store an image processing module 115 configured to interpret and compare images from an imaging system 110 (e.g., an ultrasonic imaging system). Image processing module 115 is configured to collect or receive images obtained using an ultrasound (US) probe 128. The US probe 128 may include a transrectal US (TRUS) probe (2D or 3D) as the present principles will be illustratively described in terms of a high-dose-rate (HDR) brachytherapy procedure. The probe 128 may employ an optically tracked US probe, an EM-tracked US probe, a non-tracked 3D probe, etc. The image processing module 115 may also be employed to provide functions such as manual or automatic digitization of instruments and/or organs in an imaging volume or image 134.

During a procedure, medical instruments 102, such as catheters, applicators or other instruments are inserted into a subject 160 (e.g., a patient) and in particular an organ 164 such as a prostate, etc. In a brachytherapy application, the instruments 102 are passed through a guidance grid 162. The guidance grid 162 may be calibrated/registered with a coordinate system 135 of the imaging system 110 in advance of a procedure (i.e., a priori). The instruments 102 are configured to include or receive tracking devices 104 therein, e.g., EM tracking, etc. The catheters 102, which are hollow tubes, are inserted into the tissue (subject 160 or organ 164). Then, a shape reconstructing device or tracking device 104, such as an EM-tracked guidewire is inserted into the catheters 102 and removed. In fact, one EM-tracked guidewire can be used to reconstruct the shape of several catheters. In other embodiments, the catheters 102 and the shape-reconstructing sensors or tracking devices 104 may also be integrated together.

For EM tracking, positions of the instruments 102 are tracked using the field generator 122 and a tracking system processing module 124 (e.g., for EM tracking). The EM field is generated, and the movements of the instruments 102 are tracked in an EM coordinate system 126. Other tracking systems that employ a field generator may also be employed.

In accordance with one embodiment, EM-tracked catheter positions from the EM processing module 124 are registered onto the US volume in the image processing module 115 using a registration module 136, and, hence, localize the catheters 102 in the US volume. EM signals are employed to determine the positions of the instruments 102. The instruments 102 preferably include catheters but may include a guidewire, a probe, an endoscope, other medical component, etc.

In one embodiment, workstation 112 includes a display 118 for viewing internal images of the subject (patient) 160 and may include the image 134 of the volume as an overlay of another image or rendering. Display 118 may also permit a user to interact with the workstation 112 and its components and functions, or any other element within the system 100. This is further facilitated by an interface 120, which may include a keyboard, mouse, a joystick, a haptic device, or any other peripheral or control to permit user feedback from and interaction with the workstation 112.

Memory 116 may store the registration module 136 for registering one or more US volumes or images 134 to tracked representations of catheters 102. Memory 116 also includes a planning module 142 for planning a procedure, such as an HDR prostate brachytherapy procedure or the like. The planning module or planner 142 computes dwell positions and times using catheter positions and delineations of organs of interest in the ultrasound coordinate system as part of the plan or at any time during the procedure to update the plan. The dose and amount of dwell time may be computed for high dose rate (HDR) brachytherapy or any other procedure. One benefit of the EM-US registration method is that after the registration, both catheters and the organ contours can be in the same coordinate system and can be used for tracking.

In one embodiment, a 3D transrectal US (TRUS) probe (128) is employed for imaging a prostate (164) during the delivery of radiation. The probe and/or the grid 162 may be coupled to a stepper motor 166 (stepper), which advances or otherwise positions these devices in accordance with the treatment plan. The treatment plan is also sent to an afterloader 146, which then controls the delivery of radioactive sources along the guide tubes into the pre-specified positions within the catheters 102. The sources remain in place for a pre-specified dwell time, following the treatment plan. The sources are returned along the tubes to the afterloader 146.

In one embodiment, a database or data storage structure 138 is created in memory 116. The data storage structure 138 may include a look-up table or other data structure to provide indexed information. The structure 138 includes multiple calibrations, each performed at a different position and/or orientation of the FG 122. The calibrations are associated with positions of the FG 122 and/or positions of the FG 122 relative to a reference sensor or sensors. The positions are selected based on a number of present conditions such as patient anatomical features, patient size (girth), operating room configurations, etc. Based upon these or other criteria, a position of the FG 122 may be selected, and the structure 138 can be consulted to determine calibration information. Each calibration can be tagged with the position and orientation of a 6 DOF reference sensor 144 that is attached in a repeatable static location such as on the stepper 166.

The workflow for populating the data structure 138 is preferably performed prior to the interventional procedure, as a one-time process. The calibration procedure/population of the data structure 138 may be repeated whenever desired (e.g., monthly) to update the calibration database or structure 138, if it is determined that the quality of the EM-US fusion or other registration process during the interventional procedure is not adequate.

Memory 116 includes a calibration selection module 140. The calibration selection module 140 employs calibration information to select a best calibration based upon a selected position for the FG 122. The calibration selection module 140 automatically selects the optimal calibration, after the FG 122 has been placed at the desired position/orientation at a beginning of an interventional procedure. This can be continuously or intermittently updated during a procedure. In one embodiment, calibration selection module 140 permits user-initiated selection of the calibration information (e.g., through interface 120) from the database or structure 138. This may be instead of an automatic calibration or based upon user preference, etc.

Figure 2:
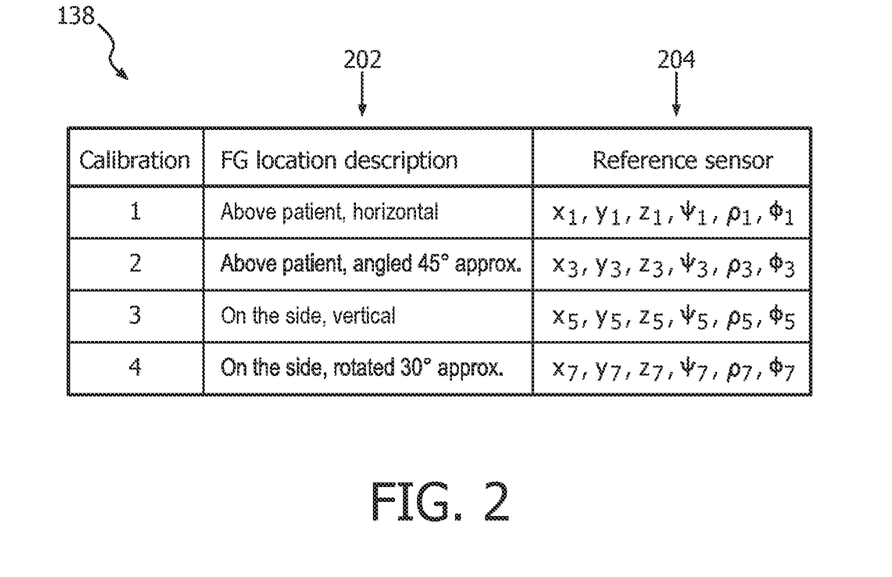
FIG. 2 is a table showing a data structure having entries for positions and orientations of a reference sensor corresponding to positions of the field generator in accordance with one illustrative embodiment.

Referring to FIG. 2, an example of the calibration database or data structure 138 is illustratively shown. The data structure 138 includes four illustrative calibrations (numbered 1-4), each corresponding to a location of the FG 122 described in column 202. At the listed FG locations in column 202, a position and an orientation of a 6 DOF reference sensor (144) are entered in the data structure 138 at column 204. While only four calibrations are shown in FIG. 2, the data structure 138 may include tens to hundreds of calibrations, each corresponding to small changes in FG position/orientation. It should also be understood that the column structure and/or relative setup of the data structure 138 may be configured in any suitable manner.

In other embodiments, the calibration look up table 138 may be filled with different calibrations for different positions of a probe tracking sensor (on a probe instead of a fixed reference sensor), and the optimal calibration may also be selected or interpolated using probe sensor information (position of the probe sensor with respect to the FG). The calibration may be interpreted between reference positions in the same manner as described above.

Figure 3:
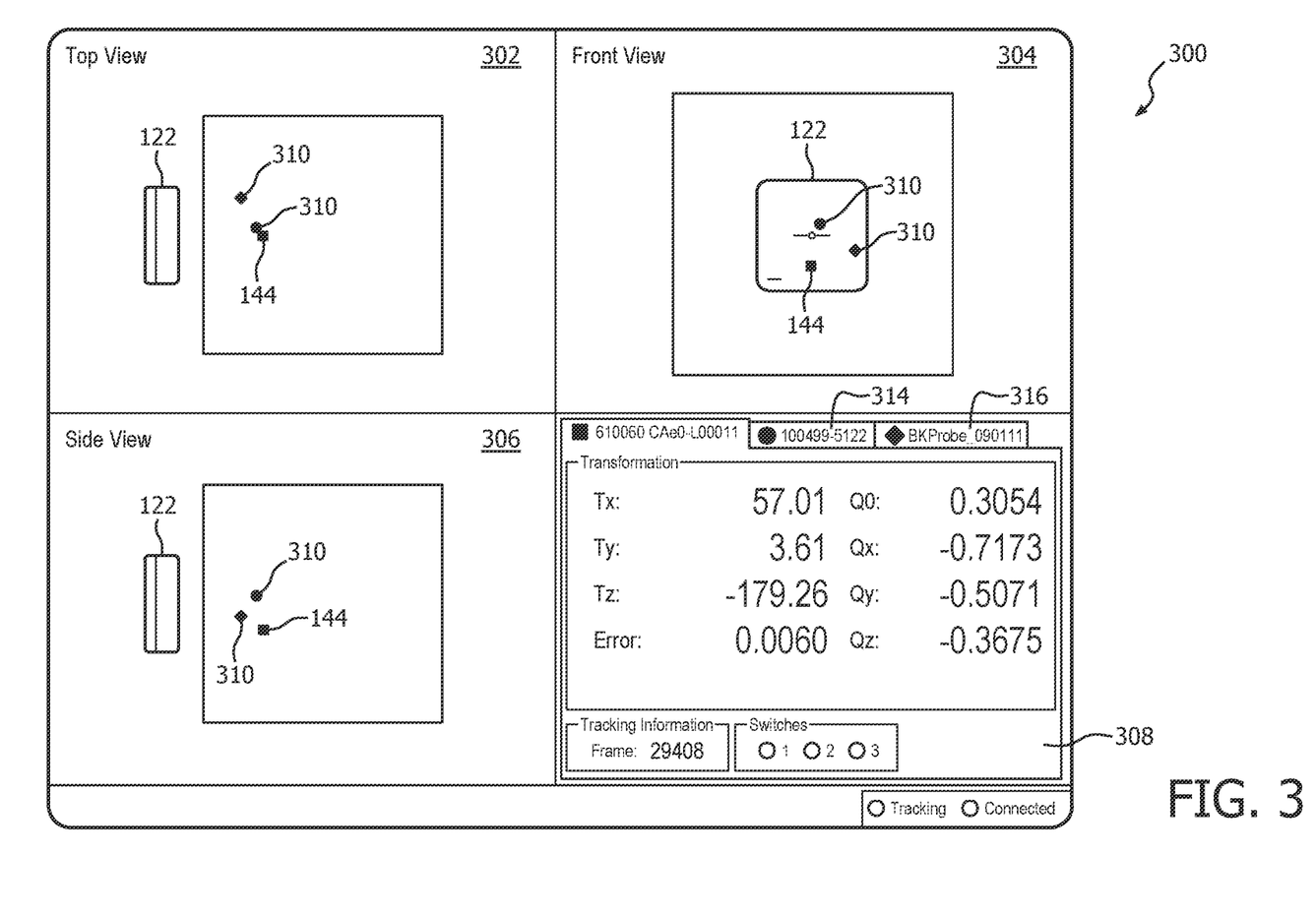
FIG. 3 is a diagram showing different views of relative position and orientation between a field generator and a reference sensor at a first position in accordance with one illustrative embodiment.

Referring to FIG. 3, a diagram shows a display screen image 300 with four view panes 302, 304, 306 and 308. The view panes 302, 304 and 306 each include a representation of the FG 122. View pane 302 shows a top view of an operating environment; view pane 304 shows a front view of the operating environment; and view pane 306 shows a side view of the operating environment. The view panes 302, 304 and 306 show the position and orientation of a reference sensor 144, for a location of the FG 122. Also depicted are dots 310, which represent other EM sensors in the field of the FG 122.

View pane 308 shows calibration information for the position of the FG 122. Namely, registration transforms, Tx, Ty, Tz, for translations, registration transforms, Qo, Qx, Qy and Qz for rotations and error information are provided for the reference sensor 144 (and for the other sensors, which are displayed upon clicking tabs 314 and 316). Registration transforms are calibrated at each position of the FG 122 and its respective reference sensor 144. In particularly useful embodiments, the reference sensors may be maintained in a common reference position for all positions of the FG 122. For example, the stepper motor 166 (FIG. 1) may include a reference platform 168. Other reference positions may also be included and employed to provide a stable reference position for multiple or all reference sensor positions.

Figure 4:
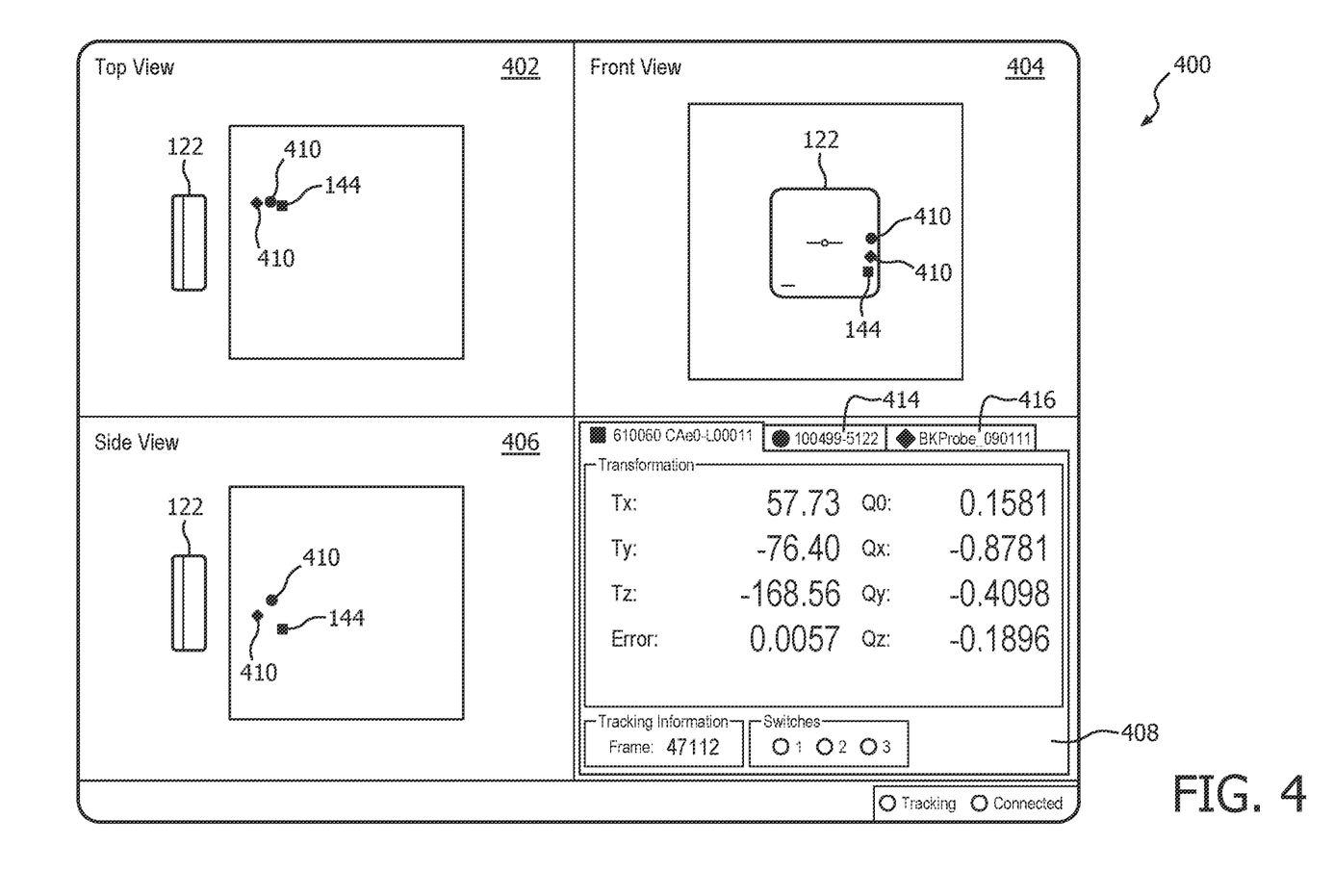
FIG. 4 is a diagram showing different views of relative position and orientation between a field generator and a reference sensor at a second position in accordance with one illustrative embodiment.

Referring to FIG. 4, another diagram shows a display screen image 400 with four views panes 402, 404, 406 and 408. The view panes 402, 404 and 406 each include a representation of the FG 122 at a second location or orientation. View pane 402 shows a top view of an operating environment; view pane 404 shows a front view of the operating environment; and view pane 406 shows a side view of the operating environment. The view panes 402, 404 and 406 show the position and orientation of the reference sensor 144, for the second location of the FG 122. Also depicted are dots 410, which represent other EM sensors in the field of the FG 122. View pane 408 shows calibration information for the position of the FG 122.

As in FIG. 3, FIG. 4 shows calibration information for the position of the FG 122 in view pane 408. Namely, registration transforms, Tx, Ty, Tz, for translations, registration transforms, Qo, Qx, Qy and Qz for rotations and error information are provided for the reference sensor 144 (and for the other sensors, which are displayed upon clicking tabs 414 and 416). Registration transforms are calibrated at each position of the FG 122 and its respective reference sensor 144. In particularly useful embodiments, the reference sensors may be maintained in a common reference position for all positions of the FG 122. For example, the stepper motor 166 (FIG. 1) may include a reference platform 168. Other reference positions may also be included and employed to provide a stable reference position for multiple or all reference sensor positions.

The data collected for the reference sensor positions in FIGS. 3 and 4 may be employed for deriving the coordinates stored in the data structure 138. The transforms may be employed directly or coordinates for a global coordinate system may be derived for storage in the data structure 138.

Referring again to FIG. 1, calibration selection module 140 is employed to automatically select the optimal calibration before or during an interventional procedure. The FG 122 is first placed at a desired position/orientation at the beginning of an interventional procedure. The position is selected based upon operator's choice or other criteria considering things such as patient size, operating room equipment, etc. In one embodiment, the process for choosing an optimal calibration is triggered by the user/operator through the interface 120. This may include, for example, clicking a virtual button, entering a command, etc. In another embodiment, the process of choosing an optimal calibration may be a continuous, real-time process. This can account for any change in FG position/orientation (either intentionally or inadvertently) during an interventional procedure. A warning message may be provided to the user every time the calibration needs to be changed. The warning message may be provided on the display 118 or on an output device 170, such as a speaker, a light, a buzzer, a vibratory output, etc., as an indication that the geometry has changed.

The optimal calibration is selected by calibration selection module 140. The position and orientation of the reference sensor 144 are monitored. The reference sensor 144 is preferably attached in a same location as during calibration. For example, in prostate interventional procedures the reference platform 168 may be employed as a common reference. The sensor 144 can be attached to the reference platform 168 during calibration and during the interventional procedure. Note that the reference sensor 144 should also be attached at a same orientation on the reference platform 168, at all times. To ascertain a consistent orientation, the sensor 144 can have an external notch or other indicia that fits into a groove or other mating position on the reference platform 168, for example. Other ways of ensuring the correct orientation are also contemplated (e.g., aligning markings on the sensor 144 and stepper (e.g., reference platform 168), etc.).

The real-time position and orientation of the sensor 144 are matched to the tags in the database or data structure 138, and a closest match is obtained. A calibration corresponding to this tag is selected as the optimal calibration. The calibration selection module 140 may include an algorithm for selecting a closest calibration by scoring each candidate calibration tag based on an actual position and orientation against closest matches in the data structure 138. In another embodiment, the optimal calibration can be interpolated by the calibration selection module 140 between the two closest recorded calibrations. This process of determining the optimal calibration can be a continuous, real-time process or one that is triggered by user action.

The optimal calibration is then loaded into the registration module 136 to fuse two coordinate systems, e.g., to fuse EM and US data. In another embodiment for continuous optimal calibration selection, several calibration parameters can be recorded for several positions of the ultrasonic probe 128 along its path on the stepper 166, and the optimal calibration can be selected based on the probe position. This is helpful for a more accurate volume reconstruction.

In other embodiments, several calibration parameters can be employed for different reference sensor positions, and the optimal calibration can be selected based on a nearest reference position or using other criteria. In yet another embodiment, the closest match of the FG position can be computed in terms of the rotation and translation of the FG relative to the reference sensor. If the closest match to the current orientation is beyond a set threshold, it will notify the user to perform a calibration with that setup to add to the database or data structure 138. This can present the user with the choice to either continue with the closest match or adjust the FG positioning to find a better match. This can be used for extreme positioning cases in which even the closest matched calibration is too geometrically different to produce accurate results.

The accuracy of EM-tracked systems is highly dependent on the position and angulation of the EM FG 122. The current lack of robustness in conventional systems and requirements for intricate calibration steps limit widespread uptake of any upcoming commercial products utilizing EM tracking. The present principles provide a system that is robust with regard to FG positioning in clinical set-ups. The present systems and methods ensure high accuracy while being insensitive to FG location. The present principles are particularly useful for all EM-tracked multi-modality systems.

Figure 5:
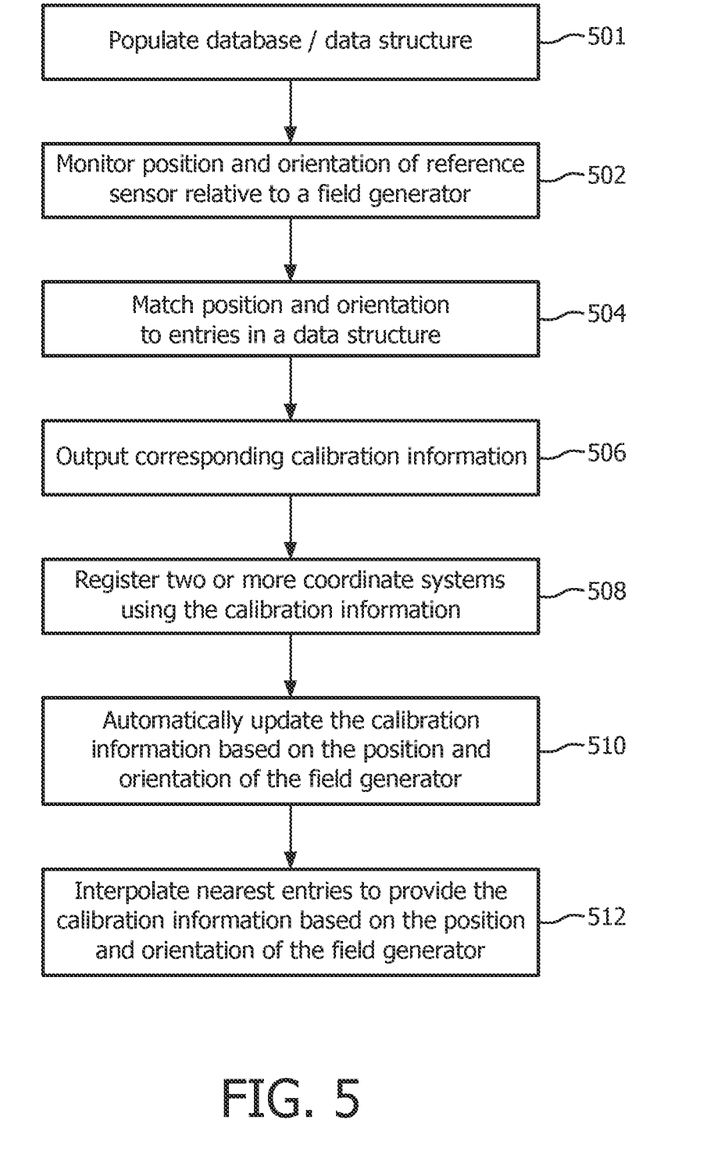
FIG. 5 is a block/flow diagram showing a method for calibrating a field generator in accordance with illustrative embodiments.

Referring to FIG. 5, a method for selecting a calibration for a field generator position is shown in accordance with illustrative embodiments. In block 501, a data structure is populated with calibration information in accordance with the position and orientation of the field generator. In block 502, a position and orientation of a reference sensor relative to a field generator is monitored.

In block 504, the position and orientation of the reference sensor are matched to a calibration entry stored in a data structure. The data structure includes non-transitory computer readable storage media. The data structure includes a plurality of calibration entries corresponding to different possible positions and orientations of the field generator with respect to the reference sensor or of the reference sensor with respect to the field generator. The entries include information for six degrees of freedom for relative positions between the field generator and the reference sensor. In one embodiment, the reference sensor is located at a fixed location for all the entries. In some embodiments, different fixed or non-fixed (e.g., on a probe) positions may be included with associated calibration information. The field generator may be placed in accordance with at least one of: operator preference, patient anatomy, equipment in the environment and conditions in the environment.

In block 506, corresponding calibration information stored in the data structure is output. The calibration information is optimized based upon the position and orientation of the field generator, that is, the best calibration information is selected for a particular the position and orientation of the field generator. The field generator is configured for placement in an environment for sensor tracking, and is configurable to permit adjustment of its position and orientation as needed.

In block 508, at least two coordinate systems are registered. The coordinate systems are registered using the chosen calibration information. The coordinate systems may include a coordinate system for sensor tracking and/or a coordinate system for an imaging modality.

In block 510, a calibration may be updated automatically (continuously or intermittently) in accordance with the position and orientation of the field generator. In other embodiments, updates may be user-initiated. In block 512, if an entry for a position and orientation of the field generator is not present in the data structure, the system interpolates between nearest calibration entries in the data structure.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for systems and methods for automated selection of optimal calibration in tracked interventional procedures (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for selecting a calibration, comprising:
a data structure including non-transitory computer readable storage media having entries for a plurality of calibrations stored therein each calibration performed at a different position and orientation of a field generator, and indexed to the position and orientation of the field generator, relative to a reference sensor, the field generator being configured for placement at a desired location in an environment for sensor tracking; and
a calibration selection module configured to determine the position and orientation of the field generator located at the desired location relative to the reference sensor, and based on the determined position and orientation, select, using the data structure, entries for the corresponding calibration stored in the data structure.

2. The system as recited in claim 1, wherein the plurality of calibrations include information for six degrees of freedom of the reference sensor.

3. The system as recited in claim 2, wherein the reference sensor is located at a same fixed location for each calibration.

4. The system as recited in claim 1, further comprising a registration module configured to register at least two coordinate systems including at least one coordinate system for the sensor tracking.

5. The system as recited in claim 4, further comprising an imaging modality wherein images collected by the imaging modality are registered with the coordinate system for the sensor tracking.

6. The system as recited in claim 1, wherein the field generator is placed in accordance with at least one of operator preference, patient anatomy, equipment in the environment or conditions in the environment.

7. The system as recited in claim 1, wherein the calibration selection module updates a calibration in accordance with the position and orientation of the field generator.

8. The system as recited in claim 1, wherein the calibration selection module interpolates between the nearest calibration in the data structure if an calibration for a position and orientation of the field generator is not present in the data structure.

9. The system as recited in claim 1, wherein the calibration selection module permits a user-initiated calibration update.

10. The system of claim 1, further comprising a display configured to display four view panes including the corresponding calibration information in one view pane, and representations of the field generator, the reference sensor and further sensors in top, front and side views of the environment in three view panes, the corresponding calibration information including registration transforms for translations and rotations for the reference sensor and the further sensors, and wherein the registration transforms are calibrated at each position of the field generator and its respective reference sensor.

11. A method for selecting a calibration, comprising acts of:
monitoring a position and orientation of a reference sensor relative to a field generator;
matching the position and orientation of the reference sensor to a calibration stored in a data structure, the data structure including non-transitory computer readable storage media; and
outputting corresponding calibration information stored in the data structure, the calibration information including a plurality of calibrations with computed calibration information for different positions and orientations of the field generator located at a desired location in an environment.

12. The method as recited in claim 11, wherein, the entries include information for six degrees of freedom.

13. The method as recited in claim 12, wherein the reference sensor is located at a same fixed location for each calibration.

14. The method as recited in claim 11, further comprising an act of registering at least two coordinate systems including at least one coordinate system for sensor tracking and a coordinate system for an imaging modality.

15. The method as recited in claim 11, wherein the field generator is placed in accordance with at least one of operator preference, patient anatomy, equipment in the environment or conditions in the environment.

16. The method as recited in claim 11, further comprising an act of updating a calibration in accordance with the position and orientation of the field generator.

17. The method as recited in claim 11, further comprising an act of interpolating between nearest calibrations in the data structure if a calibration for a position and orientation of the field generator is not present in the data structure.

18. The method as recited in claim 11, further comprising an act of populating the data structure with calibration information in accordance with the different positions and orientations of the field generator.

19. The method of claim 11, further comprising and act of displaying on a display four view panes including the corresponding calibration information in one view pane, and representations of the field generator, the reference sensor and further sensors in top, front and side views of the environment in three view panes, the corresponding calibration information including registration transforms for translations and rotations for the reference sensor and the further sensors, and wherein the registration transforms are calibrated at each position of the field generator and its respective reference sensor.

* * * * *